United States Patent [19]

Eshima et al.

[11] Patent Number: 4,870,078
[45] Date of Patent: Sep. 26, 1989

[54] W-AMINO ALKYLSULFONATE DERIVATIVES FOR IMPROVING MICROCIRCULATION

[75] Inventors: Kiyoshi Eshima; Kazuo Ogawa; Shigeru Kaneko, all of Tokushima, Japan

[73] Assignee: Taiho Pharmaceutical Co., Ltd., Tokyo, Japan

[21] Appl. No.: 193,522

[22] PCT Filed: Aug. 15, 1989

[86] PCT No.: PCT/JP87/00611
§ 371 Date: Apr. 4, 1988
§ 102(e) Date: Apr. 4, 1988

[87] PCT Pub. No.: WO88/01268
PCT Pub. Date: Feb. 25, 1988

[30] Foreign Application Priority Data

Aug. 20, 1986 [JP] Japan ................................ 61-196213

[51] Int. Cl.⁴ ................ A61K 31/495; C07D 295/08; C07D 295/20
[52] U.S. Cl. ...................................... 514/255; 544/394
[58] Field of Search ........................ 544/394; 514/255

[56] References Cited

U.S. PATENT DOCUMENTS 4,616,086 10/1986 Witte et al. ........................ 544/400

FOREIGN PATENT DOCUMENTS 72575 4/1983 Japan .

Primary Examiner—Cecilia Shen
Attorney, Agent, or Firm—Armstrong, Nikaido, Marmelstein, Kubovcik & Murray

[57] ABSTRACT

The present invention provides a taurine-type compound of the formula

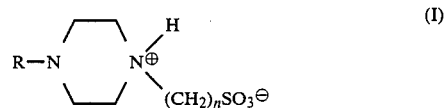

wherein R is a phenyl group optionally having substituent(s) selected from lower alkyl, halogen-substituted lower alkyl, lower alkoxy, lower alkanoyl and halogen atom; and n is 2 or 3. The above compound is useful as an agent for improving microcirculation.

12 Claims, No Drawings

W-AMINO ALKYLSULFONATE DERIVATIVES FOR IMPROVING MICROCIRCULATION

DESCRIPTION

1. Technical Field

This invention relates to a novel taurine-type compound.

2. Prior Art

Since the lumen diameter of blood vessels is regarded as one of the factors which have great influence on blood flow, vasodilators are used. However, the lumen diameter of blood vessels with arteriosclerosis, etc. is less responsive to drugs, and smooth muscle does not exist in microvessels. Further, from the standpoint of rheology, unless a pressure gradient is varied, blood flow is not sufficiently improved even if lumen diameter of vessels is changed. Therefore, for the improvement of microcirculation under ischemic condition, treatment with vasodilators alone is not expected to produce sufficient effect. Rather, it is very important to positively improve hematological properties from the standpoint of promoting the deformability of erythrocytes and of controlling platelet functions. Thus, therapies for thrombosis or microcirculation disorder from this standpoint have been attaching attention in recent years, and the investigation of the conventional agents for cardiovascular system from hemorheological standpoint has revealed that pentoxifylline, trapidil and dilazep are useful as drugs for improving hematological properties as well.

However, few agent have been developed so far which put stress on the promotion of deformability of erythrocytes and the control of platelet function that have significant hemorheological influence on the flow within microvessels. Therefore, agents that display excellent effects thereon have been demanded.

DISCLOSURE OF THE INVENTION

The main object of the present invention is to satisfy the above demand.

That is, the invention provides agents which can accelerate deformability of erythrocytes and control platelet function to thereby improve microcirculation.

We conducted extensive research on compounds having said effects, and found that certain taurine-type compounds can fulfil the above object, and accomplished the present invention.

The present invention provides a taurine-type compound represented by the formula

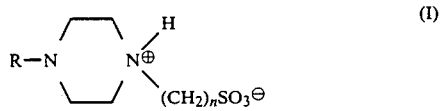

wherein R is a phenyl group optionally having substituent(s) selected from lower alkyl, halogen-substituted lower alkyl, lower alkoxy, lower alkanoyl and halogen atom, and n is 2 or 3.

The taurine-type compounds of the present invention are novel compounds undisclosed in any literatures. They not only have extremely strong effect of improving erythrocyte deformability when compared with conventional agents, but also possess inhibitory effect on platelet aggregation, and thus exert remarkable effect of improving hematological properties and are useful as medicaments for mammals including humans.

That is to say, the compounds (I) of the present invention have an excellent effect of promoting erythrocyte deformability and effect of inhibiting platelet aggregation, and improve blood fluidity in microcirculatory regions, i.e., microcirculation. Therefore, the compounds (I) of the present invention are useful as agents for preventing and treating arterioclerosis, cerebral infarction, myocardial infarction, peripheral thrombosis and obstruction, etc.

Thus the present invention also provides an agent for the improvement of microcirculation which contains an effective amount of the compound of the above formula (I) and a pharmaceutically acceptable carrier or excipient.

Further the present invention provides a method of improving microcirculation in a patient in need of amelioration of microcirculation comprising administering an effective amount of the compound of the formula (I) to said patient.

Throughout the specification and particularly in the definition of the formula (I), lower alkyl and alkyl moiety of halogen-substituted lower alkyl, lower alkoxy and lower alkanoyl are intended to mean straight or branched saturated hydrocarbon chains having 1 to 6 carbon atoms or alicyclic saturated hydrocarbon groups having 3 to 6 carbon atoms. Examples thereof are methyl, ethyl, propyl, cyclopropyl, isopropyl, butyl, isobutyl, sec-butyl, tert-butyl, cyclobutyl, pentyl, isopentyl, neopentyl, tert-pentyl, cyclopentyl, hexyl, isohexyl, cyclohexyl, etc. Examples of halogen atoms are fluorine, chlorine, bromine and the like. When R in the formula (I) is a phenyl group having substituents, the number of the substituents is preferably 1 to 3.

Among the compounds of the formula (I), preferable are those wherein R is a phenyl group optionally having one or two substituents selected from $C_1$-$C_4$ alkyl, halogen-substituted $C_1$-$C_4$ alkyl, $C_1$-$C_4$ alkoxy, $C_1$-$C_4$ alkanoyl and halogen atom. More preferable are the compounds of the formula (I) wherein R is a phenyl group optionally having one or two substituents selected from $C_1$-$C_4$ alkyl, $C_1$-$C_2$ alkoxy, chlorine atom and fluorine atom, and n is 3.

The compounds (I) of the present invention can be prepared by various processes. The typical processes are illustrated below.

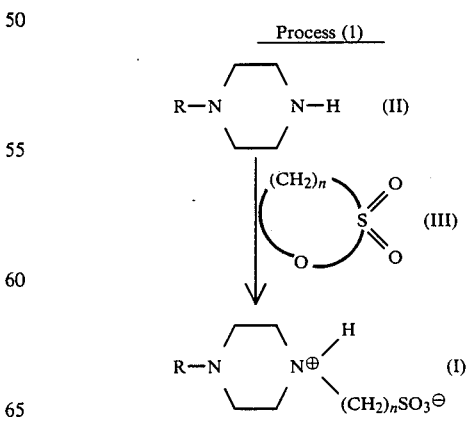

In the above reaction scheme, R and n are as defined above.

The starting material, i.e., a phenylpiperazine derivative (II) is prepared according to the method described in the following literatures:

(i) C. B. Pollard et al., J. Am. Chem. Soc., 56, 2199 (1934)
(ii) the same author et al, the same literature as above, 76, 1853 (1954)
(iii) the same author et al, J. Org. Chem., 23, 1333 (1958)

The compound of the present invention is prepared by adding a cyclic sulfonic acid ester (III) in an equimolar or slightly excess amount, relative to the phenylpiperazine derivative (II) prepared by the method described in the above literatures, to a solution of the phenylpiperazine derivative (II) in a lower alcohol, preferably methanol, ethanol, propanol and isopropanol, di-lower alkyl ketone, preferably acetone, methyl ethyl ketone and diethyl ketone or a mixture of these solvents at a temperature between 0° C. and room temperature, and then effecting the reaction by stirring the mixture at a temperature between room temperature and reflux temperature for several hours to several days. The compound of the present invention thus obtained is isolated by filtering a precipitate formed spontaneously or by filtering a precipitate formed either upon concentrating the reaction mixture by evaporating the solvent under reduced pressure or upon adding a solvent in which the reaction product is sparingly soluble. The precipitate is purified by recrystallization from water, methanol, ethanol, propanol, isopropanol, acetone, methyl ethyl ketone, diethyl ketone or a mixture of these solvents.

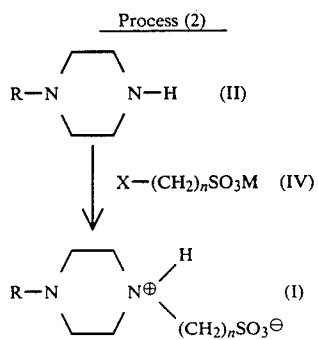

In the above reaction scheme, X is a halogen atom, M is an alkali metal or alkaline earth metal, preferably sodium or potassium, and R and n are as defined above.

The compound of the present invention is prepared by reacting the phenylpiperazine derivative (II) with equimolar or slightly excess amount of the sulfonic acid derivative (IV) in water or in a solvent which is a mixture of water and the solvent exemplified in connection with Process (1) in arbitrary proportions for several hours to several days at a temperature between room temperature and reflux temperature of the solvent used. The compound of the present invention thus obtained is isolated and purified in the same manner as described in Process (1).

The compound of the present invention may be administered orally in such dosage forms as tablets, pills, capsules, granules, powders, liquids, etc, or pareterally in such dosage forms as injections including intravenous, intramuscular and like injections, suppositories, etc.

Each of these dosage forms can be prepared by formulation methods which are conventional in the art. In preparing oral solid pharmaceutical compositions, vehicles and, if required, binders, disintegrants, lubricants, coloring agents, sweetening agents, flavors, etc. may be added to the active principle of the invention, and then tablets, coated tablets, granules, powders, capsules, etc. may be prepared by a conventional method. In preparing injections, to the active component of the present invention may be added pH adjusting agent, buffer, stabilizers, isotonic agents, local anesthetics, etc., and then subcutaneous, intramuscular, intravenous and like injections may be prepared by a conventional method. In preparing suppositories, to the active component of the present invention may be added bases and, if required, surfactants, etc., and then suppositories can be prepared according to a conventional method.

In preparing tablets, capsules, granules and powders, useful vehicles include lactose, sucrose, starch, talc, magnesium stearate, calcium stearate, crystalline cellulose, methyl cellulose, carboxymethyl cellulose, glycerin, sodium alginate, arabic gum, etc; useful binders include polyvinyl alcohol, polyvinyl ether, ethyl cellulose, arabic gum, shellac, sucrose, etc; useful lubricants include magnesium stearate, talc, etc.; coloring agents and disintegrants can be those commonly used in this field. Tablets may be coated by a conventional method.

Bases to be used in preparing suppositories include oleaginous bases such as cacao butter, polyethyleneglycol, lanolin, fatty acid triglycerides, Witepsol (registered trademark, product of Dynamite Nobel).

In the pharmaceutical compositions of the invention, the content of the compound of the present invention may vary according to dosage form, solubility of the compound, chemical properties, administration route, dosage plan, etc. Generally, the content is preferably about 10-15 w/w% in oral compositions (tablets, capsules, etc.), about 0.1-1 w/v% in injections, and about 1-5 w/w% in suppositories.

The dose of the compound of the formula (I) of the present invention is appropriately determined case by case depending on symptoms, age and sex of subjects, etc. When administered orally, a daily dose of about 1 to about 300 mg is generally given to human adults in 2-4 divided doses. When administered in the form of injection, for example, intravenous injection, a dose of 2 ml (1-10 mg), which may be diluted with saline or glucose solution for injection if required, is generally injected gradually to human adults over 5 minutes or more once a day. In the case of suppositories, a daily dose of 1-300 mg is generally inserted intrarectally to human adults once or twice a day at intervals of 6-12 hours.

The present invention will be described in greater detail with reference to the following examples and pharmacological tests.

EXAMPLE 1

4-(3-Sulfopropyl)-1-(p-tolyl)piperazine, inner salt (Compound 1)

A 1.48 g quantity (8.40 mmols) of 1-(p-tolyl)piperazine is dissolved in 30 ml of ethanol and the solution is ice-cooled. A solution of 1.22 g (10 mmols) of 1,3-propanesultone in 10 ml of acetone is slowly added dropwise with stirring. The mixture is stirred with ice-cooling for one hour and subsequently stirred at room temperature overnight to effect reaction, and then 50 ml of acetone is added thereto. The crystals precipitated are collected by filtration and recrystallized from water-methanol-acetone.

Yield: 1.3 g (52%).

M.p.: 268°–270° C. (decomp.).

TLC: Rf=0.33 (silica gel; chloroform/methanol=3/1 (v/v)).

IR spectrum (KBr tablet): 1160 cm$^{-1}$ ($\nu_{SO_2}$ (asymmetric)), 1030 cm$^{-1}$ ($\nu_{SO_2}$ (symmetric)).

FAB mass spectrum (m/e): 299 (M+1).

$^1$H-NMR spectrum (DMSO-d$_6$, TMS as an internal standard, δ), 2.01 (2H, quintet, J=6.8 Hz, —CH$_2$—), 2.21 (3H, singlet, —CH$_3$), 2.5–4.0 (12H, multiplet, —CH$_2$—), 6.9 (2H, doublet, J=8.7 Hz, φ-H), 7.1 (2H, doublet, J=8.7 Hz, φ-H), 9.9 (1H, broad singlet, >N$^⊕$H).

Elemental analysis (for C$_{14}$H$_{22}$N$_2$S$_1$O$_3$, MW=298.40): Calculated value (%): H, 7.43; C, 56.35; N, 9.39. Found value (%): H, 7.74; C, 56.12; N, 9.27.

EXAMPLE 2

4-(3-Sulfopropyl)-1-phenylpiperazine, inner salt (Compound 2)

Using 3.25 g (20 mmols) of 1-phenylpiperazine and 2.44 g (20 mmols) of 1,3-propanesultone, the reaction is conducted in the same manner as in Example 1, and the resulting crude crystals are recrystallized from water.

Yield: 1.4 g (25%).

M.p.: decomposition at 260° C. or higher.

TLC: Rf=0.23 (silica gel; chloroform/methanol=3/1 (v/v)).

IR spectrum (KBr tablet): 1155 cm$^{-1}$ ($\nu_{SO_2}$ (asymmetric)), 1030 cm$^{-1}$ ($\nu_{SO_2}$ (symmetric)).

FAB mass spectrum (m/e): 285 (M+1).

$^1$H-NMR spectrum (DMSO-d$_6$, TMS as an internal standard, δ), 2.00 (2H, quintet, J=6.8 Hz, —CH$_2$—), 2.64 (2H, triplet, J=6.8 Hz, —CH$_2$—), 3.0–3.5 (10H, multiplet, —CH$_2$—), 6.5–7.0 (3H, multiplet, φ-H), 7.19 (2H, multiplet, φ-H).

Elemental analysis (for C$_{13}$H$_{20}$N$_2$S$_1$O$_3$, MW=284.37): Calculated value (%): H, 7.09; C, 54.91; N, 9.85. Found value (%): H, 7.38; C, 55.19; N, 10.06.

EXAMPLE 3

4-(2-Sulfoethyl)-1-phenylpiperazine, inner salt (Compound 3)

A 3.25 g quantity (20 mmols) of 1-phenylpiperazine is dissolved in 10 ml of water, and a solution of 4.3 g (20 mmols) of sodium 2-bromoethanesulfonate in 10 ml of water is added dropwise thereto at room temperature with stirring. The mixture is subjected to reaction at room temperature for 1 hour and then at 70° C. overnight, and cooled. The crystals precipitated are collected by filtration and recrystallized from water-acetone.

Yield: 1.8 g (33%).

M.p.: decomposition at 250° C. or higher.

TLC: Rf=0.12 (silica gel; chloroform/methanol=3/1 (v/v).

IR spectrum (KBr tablet): 1170 cm$^{-1}$ ($\nu_{SO_2}$ (symmetric)), 1050 cm$^{-1}$ ($\nu_{SO_2}$ (symmetric)).

FAB mass spectrum (m/e): 271 (M+1).

$^1$H-NMR spectrum (DMSO-d$_6$, TMS as an internal standard, δ): 2.8–3.5 (12H, multiplet, —CH$_2$—), 6.7–7.0 (3H, multiplet, φ-H), 7.26 (2H, multiplet, φ-H).

Elemental analysis (for C$_{12}$H$_{18}$N$_2$S$_1$O$_3$, MW=270.35): Calculated value (%): H, 6.71; C, 53.31; N, 10.36. Found value (%): H, 7.06; C, 52.98; N, 10.20.

EXAMPLE 4

4-(3-Sulfopropyl)-1-(p-acetylphenyl)piperazine, inner salt (Compound 4)

A 4.1 g quantity (20 mmols) of 1-(p-acetylphenyl)piperazine is dissolved in 40 ml of acetone, and a solution of 2.44 g (20 mmols) of 1,3-propanesultone in 10 ml of acetone is added dropwise thereto at room temperature with stirring. After reaction at room temperature with stirring overnight, the yellow crystals precipitated are collected by filtration and then recrystallized from water-acetone.

Yield: 1.7 g (26%).

M.p.: decomposition at 250° C. or higher.

TLC: Rf=0.10 (silica gel; chloroform/methanol=3/1 (v/v).

IR spectrum (KBr tablet): 1650 cm$^{-1}$ ($\nu_{C=O}$), 1150 cm$^{-1}$ ($\nu_{SO_2}$ (asymmetric)), 1030 cm$^{-1}$ ($\nu_{SO_2}$ (symmetric)).

FAB mass spectrum (m/e): 327 (M+1).

$^1$H-NMR spectrum (DMSO-d$_6$, TMS as an internal standard, δ):

1.98 (2H, quintet, J=6.8 Hz, —CH$_2$—), 2.47 (3H, singlet, CH$_3$CO—), 2.64 (2H, triplet, J=6.8 Hz, —CH$_2$—), 2.8–3.5 (10H, multiplet, —CH$_2$—), 7.04 (2H, doublet, J=8.7 Hz, φ-H), 7.82 (2H, doublet, 8.7 Hz, φ-H).

Elemental analysis (for C$_{15}$H$_{22}$N$_2$S$_1$4, MW=326.41): Calculated value (%): H, 6.79; C, 55.20; N, 8.58. Found value (%): H, 7.02; C, 54.95; N, 8.66.

EXAMPLE 5

4-(3-Sulfopropyl)-1-(p-fluorophenyl)piperazine, inner salt (Compound 5)

The reaction is conducted in the same manner as in Example 4 except that 5.2 g (29 mmols) of 1-(p-fluorophenyl)piperazine and 3.5 g (29 mmols) of 1,3-propanesultone are used. The resulting product is recrystallized from ethanol.

Yield: 2.5 g (29%).

M.p.: 265°–268° C. (decomp.).

TLC: Rf=0.18 (silica gel; chloroform/methanol=3/1 (v/v).

IR spectrum (KBr tablet): 1165 cm$^{-1}$ ($\nu_{SO_2}$ (asymmetric)), 1025 cm$^{-1}$ ($\nu_{SO_2}$ (symmetric)).

FAB mass spectrum (m/e): 303 (M+1).

$^1$H-NMR spectrum (DMSO-d$_6$, TMS as an internal standard, δ) 2.04 (2H, quintet, J=6.8 Hz, —CH$_2$—), 2.69 (2H, triplet, J=6.8 Hz, —CH$_2$—), 2.8–4.0 (10H, multiplet, —CH$_2$—), 7.06 (4H, multiplet, φ-H), 9.9 (1H, broad singlet, >N$^⊕$H).

Elemental analysis (for C$_{13}$H$_{19}$N$_2$S$_1$O$_3$F$_1$, MW=302.37): Calculated value (%): H, 6.33; C, 51.64; N, 9.26. Found value (%): H, 6.58; C, 51.77; N, 9.25.

EXAMPLE 6

4-(3-Sulfopropyl)-1-(o-methoxyphenyl)piperazine, inner salt (Compound 6)

The reaction is conducted in the same manner as in Example 4 except that 5.0 g (26 mmols) of 1-(o-methoxyphenyl)piperazine and 3.2 g (26 mmol) of 1,3-propanesultone are used. The resulting product is recrystallized from methanol.

Yield: 6.5 g (80%).

M.p.: 271°–273° C. (decomp.)

TLC: Rf=0.38 (silica gel; chloroform/methanol=3/1 (v/v)).

IR spectrum (KBr tablet): 1160 cm$^{-1}$ ($\nu_{SO2}$ (asymmetric)), 1035 cm$^{-1}$ ($\nu_{SO2}$ (symmetric)).F AB mass spectrum (m/e): 315 (M+1).

$^1$H-NMR spectrum (DMSO-d$_6$, TMS as an internal standard, δ) 2.04 (2H, quintet, J=6.8 Hz, —CH$_2$—), 2.68 (2H, triplet, J=6.8 Hz, —CH$_2$—), 2.5-4.0 (10H, multiplet, —CH$_2$—), 3.79 (3H, singlet, —OCH$_3$), 6.7-7.3 (4H, multiplet, φ-H). 9.86 (1H, broad singlet, >N⊕H).

Elemental analysis (for C$_{14}$H$_{22}$N$_2$S$_1$O$_4$, MW=314.40): Calculated value (%): H, 7.05; C, 53.48; N, 8.91. Found value (%): H, 7.34; C, 53.22; N, 8.83.

EXAMPLE 7

4-(3-Sulfopropyl)-1-(o-trifluoromethylphenyl)piperazine, inner salt (Compound 7)

The reaction is conducted in the same manner as in Example 4 except that 5.0 g (22 mmols) of 1-(o-trifluoromethylphenyl)piperazine and 2.7 g (22 mmols) of 1,3-propanesultone are used. The resulting product is recrystallized from methanol-water.

Yield: 5.3 g (69%).
M.p.: 292°–294° C. (decomp.).
TLC: Rf=0.15 (silica gel; chloroform/methanol =3/1 (v/v)).

IR spectrum (KBr tablet): 1145 cm$^{-1}$ ($\nu_{SO2}$ (asymmetric)), 1030 cm$^{-1}$ ($\nu_{SO2}$ (symmetric)).

FAB mass spectrum (m/e): 353 (M+1).

$^1$H-NMR spectrum (DMSO-d$_6$, TMS as an internal standard, δ), 2.03 (2H, quintet, J=6.8 Hz, —CH$_2$—), 2.68 (2H, triplet, J=6.8 Hz, —CH$_2$—), 2.7-4.2 (10H, multiplet, —CH$_2$—), 7.1-7.6 (4H, multiplet, φ-H).

Elemental analysis (for C$_{14}$H$_{19}$N$_2$S$_1$O$_3$F$_3$, MW=352.37): Calculated value (%): H, 5.43; C, 47.72; N, 7.95. Found value (%): H, 5.62; C, 47.53; N, 7.97.

EXAMPLE 8

4-(3-Sulfopropyl)-1-(m-chlorophenyl)piperazine, inner salt (Compound 8)

The reaction is conducted in the same manner as in Example 4 except that 4.22 g (21.5 mmols) of 1-(m-chlorophenyl)piperazine and 2.62 g (21.5 mmols) of 1,3-propanesultone are used. The resulting product is recrystallized from water-acetone.

Yield: 4.4 g (64%).
M.p.: decomposition at 245° C. or higher.
TLC: Rf=0.17 (silica gel; chloroform/methanol =3/1 (v/v)).

IR spectrum (KBr tablet): 1150 cm$^{-1}$ ($\nu_{SO2}$ (asymmetric)), 1035 cm$^{-1}$ ($\nu_{SO2}$ (symmetric)).

FAB mass spectrum (m/e): 319 (M+1).

$^1$H-NMR spectrum (DMSO-d$_6$, TMS as an internal standard, δ) 2.03 (2H, quintet, J=6.8 Hz, —CH$_2$—), 2.67 (2H, triplet, J=6.8 Hz, —CH$_2$—), 2.5-4.0 (10H, multiplet, —CH$_2$—), 6.8-7.3 (4H, multiplet, φ-H), 9.86 (1H, broad singlet, >N⊕H).

Elemental analysis (for C$_{13}$H$_{19}$N$_2$S$_1$O$_3$Cl$_1$, MW=318.82): Calculated value (%): H, 6.01; C, 48.98; N, 8.79. Found value (%): H, 6.15; C, 49.30; N, 8.66.

EXAMPLE 9

4-(3-Sulfopropyl)-1-(p-methoxyphenyl)piperazine, inner salt (Compound 9)

The reaction is conducted in the same manner as in Example 4 except that 4.2 g (22 mmols) of 1-(p-methoxyphenyl)piperazine and 3.2 g (26 mmols) of 1,3-propanesultone are used. The resulting product is recrystallized from water-acetone.

Yield: 4.2 g (61%).
M.p.: 285°–287° C. (decomp.).
TLC: Rf=0.43 (silica gel; chloroform/methanol/water=65/25/4 (v/v/v)).

IR spectrum (KBr tablet): 1160 cm$^{-1}$ ($\nu_{SO2}$ (asymmetric)), 1030 cm$^{-1}$ ($\nu_{SO2}$ (symmetric)).

FAB mass spectrum (m/e): 315 (M+1).

$^1$H-NMR spectrum (DMSO-d$_6$, TMS as an internal standard, δ), 2.05 (2H, quintet, J=6.8 Hz, —CH$_2$—), 2.68 (2H, triplet, J=6.8 Hz, —CH$_2$—), 2.8-3.6 (10H, multiplet, —CH$_2$—), 3.7 (3H, singlet, —CH$_3$), 6.84 (2H, doublet, J=8.9 Hz, φ-H), 6.97 (2H, doublet, J=8.9 Hz, φ-H), 9.9 (1H, broad singlet, >N⊕H).

Elemental analysis (for C$_{14}$H$_{22}$N$_2$S$_1$O$_4$, MW=314.40): Calculated value (%): H, 7.05; C, 53.48; N, 8.91. Found value (%): H, 7.32; C, 53.36; N, 8.87.

EXAMPLE 10

4-(3-Sulfopropyl)-1-(3,4-dimethoxyphenyl)piperazine, inner salt (Compound 10)

The reaction is conducted in the same manner as in Example 4 except that 6.4 g (29 mmols) of 1-(3,4-dimethoxyphenyl)piperazine and 4.3 g (35 mmols) of 1,3-propanesultone are used. The resulting product is recrystallized from water-acetone.

Yield: 9.2 g (92%).
M.p.: 275°–276° C.
TLC: Rf=0.46 (silica gel; chloroform/methanol/water=65/25/4 (v/v/v)).

IR spectrum (KBr tablet): 1160 cm$^{-1}$ ($\nu_{SO2}$ (asymmetric)), 1030 cm$^{-1}$ ($\nu_{SO2}$ (symmetric)).

FAB mass spectrum (m/e): 345 (M+1).

$^1$H-NMR spectrum (DMSO-d$_6$, TMS as an internal standard, δ), 2.05 (2H, quintet, J=6.8 Hz, —CH$_2$—), 2.70 (2H, triplet, J=6.8 Hz, —CH$_2$—), 2.8-3.6 (10H, multiplet, —CH$_2$—), 3.68 (3H, singlet, —CH$_3$), 3.75 (3H, singlet, —CH$_3$), 6.4-6.9 (3H, multiplet, φ-H), 9.9 (1H, broad singlet, >N⊕H).

Elemental analysis (C$_{15}$H$_{24}$N$_2$S$_1$O$_5$, MW=344.43): Calculated value (%): H, 7.02; C, 52.31; N, 8.13. Found value (%): H, 7.22; C, 52.16; N, 8.11.

EXAMPLE 11

4-(3-Sulfopropyl)-1-(p-tert-butylphenyl)piperazine, inner salt (Compound 11)

The reaction is conducted in the same manner as in Example 4 except that 2.2 g (10 mmols) of 1-(p-tert-butylphenyl)piperazine and 1.8 g (15 mmols) of 1,3-propanesultone are used. The resulting product is recrystallized from water-methanol-acetone.

Yield: 2.2 g (65%).
M.p.: decomposition at 285° C. or higher.
TLC: Rf=0.5 (silica gel; chloroform/methanol =2/1 (v/v)).

IR spectrum (KBr tablet): 1160 cm$^{-1}$ ($\nu_{SO2}$ (asymmetric)), 1035 cm$^{-1}$ ($\nu_{SO2}$ (symmetric)).

FAB mass spectrum (m/e): 341 (M+1).

$^1$H-NMR spectrum (DMSO-d$_6$, TMS as an internal standard, δ), 1.24 (9H, singlet, —CH$_3$), 2.0 (2H, quintet, J=6.8 Hz, —CH$_2$—), 2.66 (2H, triplet, J=6.8 Hz, —CH$_2$—), 2.5-4.0 (10H, multiplet, —CH$_2$—), 6.9 (2H, doublet, J=8.9 Hz, φ-H), 7.3 (2H, doublet, J=8.9 Hz, φ-H), 9.9 (1H, broad singlet, >N⊕H).

Elemental analysis (for $C_{17}H_{28}N_2S_1O_3$, MW=340.48): Calculated value (%): H, 8.29; C, 59.97; N, 8.23. Found value (%): H, 8.53; C, 59.87; N, 8.14.

EXAMPLE 12

4-(3-Sulfopropyl)-1-(o-tolyl)piperazine, inner salt (Compound 12)

The reaction is conducted in the same manner as in Example 4 except that 4.1 g (23 mmols) of 1-(o-tolyl)-piperazine and 3.4 g (28 mmols) of 1,3-propanesultone are used. The resulting product is recrystallized from water.

Yield: 4.4 g (63%).
M.p.: 289°–291° C. (decomp.)
TLC: Rf=0.57 (silica gel; chloroform/methanol/-water=65/25/4 (v/v/v)).
IR spectrum (KBr tablet): 1150 cm$^{-1}$ ($\nu_{SO2}$ (asymmetric)), 1030 cm$^{-1}$ ($\nu_{SO2}$ (symmetric)).
FAB mass spectrum (m/e): 299 (M+1).
$^1$H-NMR spectrum (DMSO-d$_6$, TMS as in internal standard, δ) 2.05 (2H, quintet, J=6.8 Hz, —CH$_2$—), 2.26 (3H, singlet, —CH$_3$), 2.70 (2H, triplet, J=6.8 Hz, —CH$_2$—), 2.9–3.7 (10H, multiplet, —CH$_2$—), 6.94–7.23 (5H, multiplet, φ-H), 10.0 (1H, broad singlet, >N$^\oplus$H).
Elemental analysis (for $C_{14}H_{22}N_2S_1O_3$, MW=298.40): Calculated value (%): H, 7.43; C, 56.35; N, 9.39. Found value (%): H, 7.66; C, 56.21; N, 9.29.

EXAMPLE 13

4-(3-Sulfopropyl)-1-(o-chlorophenyl)piperazine, inner salt (Compound 13)

The reaction is conducted in the same manner as in Example 4 except that 4.2 g (21.4 mmols) of 1-(o-chlorophenyl)piperazine and 3.2 g (26.2 mmols) of 1,3-propanesultone are used. The resulting product is recrystallized from water.

Yield: 4.4 g (64%).
M.p.: decomposition at 290° C. or higher.
TLC: Rf=0.55 (silica gel; chloroform/methanol/-water=65/25/4 (v/v/v)).
IR spectrum (KBr tablet): 1155 cm$^{-1}$ ($\nu_{SO2}$ (asymmetric)), 1030 cm$^{-1}$ ($\nu_{SO2}$ (symmetric)).
FAB mass spectrum (m/e): 319 (M+1).
$^1$H-NMR spectrum (DMSO-d$_6$, TMS as an internal standard, δ), 2.04 (2H, quintet, J=6.8 Hz, —CH$_2$—), 2.70 (2H, triplet, J=6.8 Hz, —CH$_2$—), 2.8–3.8 (10H, broad multiplet, —CH$_2$—), 7.04–7.51 (4H, multiplet, φ—H), 10.05 (1H, broad singlet, >N$^\oplus$H).
Elemental analysis (for $C_{13}H_{19}N_2S_1O_3Cl_1$, MW=318.82): Calculated value (%): H, 6.01; C, 48.98; N, 8.79. Found value (%): H, 6.30; C, 48.83; N, 8.77.

PHARMACOLOGICAL TEST

The pharmacological tests with respect to the compounds (I) according to the present invention are described below.

(A) EFFECT ON ACCELERATION OF ERYTHROCYTE DEFORMABILITY

Experiment 1: Filter Filtration Method

A dispersion of erythrocytes used was prepared by cetrifuging heparinized venous blood of Japanese albino rabbit (1100 r.p.m.×7 minutes, at 4° C.), repeating the steps of washing the precipitate with phosphate buffered saline (140.5 mM NaCl, 8 mM Na$_2$HPO$_4$, 2 mM KH$_2$PO$_4$, pH 7.4) having a temperature of 4° C. and centrifuging the precipitate (2800 r.p.m.×10 minutes, at 4° C.) for several times, and dispersing the centrifugate in a phosphate buffered saline having a temperature of 4° C. to give a dispertion of 5%-Hct (hematocrit).

Subsequently NaCl was added to the dispersion to adjust it to a high osmotic pressure of 400 mOsm/kg. Then, time (FR) required for 0.5 ml of the dispersion of erythrocytes to pass through a filter at 37° C. under the influence of gravity was determined with or without addition of drug. The filter employed was that for determination of erythrocyte deformability (5 μm of pore diameter, 13 mmφ, product of Nomura Micro Science). The variation rate(%) calculated from the following equation was used as an index of improvement of deformability.

$$\text{Variation rate(\%)} = \frac{FR(\text{drug}) - FR(\text{control})}{FR(\text{control}) - FR(\text{blank})}$$

wherein FR(drug) stands for FR value determined with addition of drug, FR(control) stands for FR value determined without addition of drug, and FR(blank) stands for FR value of phosphate buffered saline.

The results indicate that the variation rate was −11.9% in the case of pentoxifylline (Trental ®, product of Hoechst Janan), while it was −24% in the case of 4-(3-sulfopropyl)-1-(p-tolyl)piperazine (inner salt) of the present invention (Compound 1). Therefore it is seen that the compound of the present invention remarkably improves the erythrocyte deformability.

Experiment 2: Viscosity Determination Method

Blood viscosity was determined at 37° C. at the shear rate of 150, 75, 37.5 and 18.75 sec$^{-1}$ using ELD rotational viscosimeter (product of Tokyo Keiki, 0.8° cone).

After heparinized venous blood of Japanese albino rabbit was preserved at 4° C. for 24 hours, the blood was tested with or without addition of drug (20 μg/ml).

The results indicated that Compound 1 of the present invention exerted stronger viscosity reducing effect than the controls, i.e., dilazep (Comelian ®, product of Kowa) and pentoxifylline (Trental ®, product of Hoechst Japan). The results are shown in Table 1.

TABLE 1

| Drug (20 μg/ml) | Viscosity of preserved blood (cp) | | | |
|---|---|---|---|---|
| | 150 sec$^{-1}$ | 75 sec$^{-1}$ | 37.5 sec$^{-1}$ | 18.75 sec$^{-1}$ |
| Compound 1 | 3.55 | 4.26 | 5.34 | 6.72 |
| Dilazep | 4.02 | 5.46 | 7.20 | 8.88 |
| Pentoxifylline | 4.15 | 5.64 | 8.70 | 13.4 |
| Blank | 4.26 | 5.94 | 9.00 | 16.8 |

Experiment 3: Morphological Observation

A dispersion of erythrocytes of Japanese albino rabbit (46%-Hct (hematocrit), solvent: phosphate buffered saline) was prepared in the same manner as in Experiment 1, and a drug (20 μg/ml) was added thereto. The mixture was then diluted 25-fold with phosphate buffered saline having a high osmotic pressure of 400 mOsm/kg, and observed by an optical microscope.

According to the results, when Compound 1 or 4-(3-sulfopropyl)-1-(p-fluorophenyl)piperazine, inner salt (Compound 5) or 4-(3-sulfopropyl)-1-(o-methoxyphenyl)piperazine, inner salt (Compound 6) of the present invention was added, each of these drugs exerted the effect of normalizing the shape of erythrocytes which had been made abnormal due to the high osmotic pressure. The effect was remarkably stronger than that of pentoxifylline (Trental ®, product of Hoechst Japan) serving as control, and equal or superior to that of dilazep (Comelian ®, product of Kowa) serving as control.

While pentoxifylline, trapidil and dilazep are recognized as typical agents for promoting erythrocyte deformability, the above test demonstrated that this erythrocyte deformability promoting effect of the compounds of the present invention are stronger than that of dilazep which was reported to exhibit 10 times the effect of trapidil and 100 times the effect of pentoxifylline (Susumu Yamamoto et al., Japanese Pharmacology & Therapeutics, 11(10), 4273 (1983)).

(B) INHIBITORY EFFECT OF PLATELET AGGREGATION

Platelet rich plasma (PRP) and platelet poor plasma (PPP) used were prepared from citric acid-added arterial blood of Japanese albino rabbit. The platelet aggregation test was conducted according to the method described in literature (G. V. R. Born, Nature, 194, 927 (1962)). The inhibitory effect of the drug on platelet aggregation induced independently by collagen (final concentration: 5 $\mu$g/ml) and by ADP (adenosine diphosphate, final concentration: 10 $\mu$M) were determined using aggregometer.

The results indicated that, at a concentration of 100 $\mu$g/ml, the aggregation inhibitory effects of Compounds, 1, 5 and 6 of the present invention were 1.2–2.3 times (collagen-induced) and 1.7–3.9 times (ADP-induced) as strong as dilazep (Comelian ®, product of Kowa).

(C) EFFECT ON BLOOD VISCOSITY ON DISTURBING BLOOD FLOW

The common carotid arteries and jugular veins of Wister-rats 300–370 g in body weight were exposed under anesthesia with pentobarbital. Blood sample was obtained as heparinized blood (1) from one of the veins. Then both of arteries were ligated. Sixty minutes after the ligation, the other vein was ligated, and, from the end of the vein, blood returning from the head was similarly collected as heparinized blood (2).

The percent increase in the viscosity of the heparinized blood (2) was determined based on the viscosity of the heparinized blood (1). The blood viscosity was determined immediately after blood collection using the same rotational viscosimeter as used in Experiment 2 of the above item (A) Effect on acceleration of erythrocyte deformability. The test drugs were dissloved in physiological saline and injected via tail vein 15 minutes before the ligation of the vein.

The results obtained at shear rates of 37.5, 75 and 150 sec$^{-1}$ were shown in Table 2.

In the control group which was given only physiological saline, marked increase in viscosity was observed at all shear rates of 18.75, 37.5, 75, 150 and 375 sec$^{-1}$. In contrast, as evident from the results shown in Table 2, the compound of the present invention such as 4-(3-sulfopropyl)-1-(p-tert-butylphenyl)piperazine, inner salt (Compound 11) displayed siginificant inhibitory effect on the increase in blood viscosity, which proved to be stronger than that of known agents for improving microcirculation, i.e. pentoxifylline and trapidil.

On the other hand, diltiazem which is a vasodilator was not effective in this test at a dose (0.5 mg/kg) at which this drug produce a vasodilating action.

TABLE 2

| Test drug (dosage) | Percent increase in blood viscosity Shear rate (sec$^{-1}$) | | |
|---|---|---|---|
| | 37.5 | 75 | 150 |
| Control (−) | 29.6 ± 1.8 | 22.3 ± 0.9 | 15.4 ± 0.5 |
| Compound 11 (1 mg/kg) | 15.8 ± 3.2**# | 13.0 ± 2.9* | 6.8 ± 2.3** |
| Compound 11 (10 mg/kg) | 17.8 ± 1.7**# | 14.5 ± 1.5** | 10.9 ± 1.2** |
| Pentoxifylline (10 mg/kg) | 27.8 ± 2.7 | 20.5 ± 2.1 | 13.5 ± 1.8 |
| Trapidil (10 mg/kg) | 26.0 ± 1.7 | 20.7 ± 0.3 | 14.1 ± 1.7 |
| Diltiazem (0.5 mg/kg) | 27.5 ± 0.6 | 22.6 ± 1.0 | 14.9 ± 2.3 |

(Note) Means ± S.D.
*$p < 0.05$ (in comparision with control)
**$p < 0.01$ (in comparision with control)
**#$p < 0.05$ (in comparision with pentoxifilline)

(D) EFFECT ON BLOOD PRESSURE IN ANESTHETIZED RAT

Blood pressure was determined by cannulation in the carotid artery of pentobarbital-anesthetized rat and connecting the cannula to a blood pressure transducer.

When 0.5 mg/kg of diltiazem was administered, the effect on blood pressure was observed immediately after the administraion and the blood pressure was recovered after about 20 minutes later. When 1 mg/kg or 10 mg/kg of pentoxifylline was administered, the transient dose-dependent effect on blood pressure was observed immediately after the administration.

On the other hand, it was observed that, when 1 mg/kg or 10 mg/kg of the compound of the present invention, e.g., Compound 11 was administered, the compound had substantially no influence on blood pressure, demonstrating its hemorheological effect selectively.

The following preparation examples illustrate pharmaceutical compositions containing the compound of the present invention and preparing methods thereof.

PREPARATION EXAMPLE 1

(Preparation of Tablets)

| | |
|---|---|
| Compound 11 | 50 g |
| Lactose | 200 g |
| Corn starch | 80 g |
| Hydrolyzed starch | 20 g |
| Calcium stearate | 10 g |
| | 360 g |

Compound 11, lactose, corn starch and hydrolyzed starch were mixed, and granulation was conducted after adding water thereto, giving active paste. After drying overnight at 45° C., the granules were sieved, and thereto was added calcium stearate, followed by compression, giving tablets 360 mg in weight and 10 mm in diameter.

PREPARATION EXAMPLE 2

(Preparation of Tablets)

| | |
|---|---|
| Compound 11 | 25.0 g |
| Lactose | 115.0 g |
| Corn starch | 50.0 g |
| Gelatinized corn starch | 8.0 g |
| Calcium stearate | 2.0 g |

-continued

|  |  |
|---|---|
|  | 200.0 g |

Compound 11, lactose, corn starch and gelatinized corn starch were mixed. After crushing, the mixture was made pasty by adding water. The paste was dried overnight at 45° C., mixed with calcium stearate and shaped by compression into tablets 200 mg in weight and 8 mm in diameter.

PREPARATION EXAMPLE 3

(Preparation of Capsules)

| Compound 11 | 25.0 g |
|---|---|
| Lactose | 150.0 g |
| Corn starch | 40.0 g |
| Talc | 5.0 g |
|  | 220.0 g |

Compound 11, lactose and corn starch were mixed and crushed. After mixing with talc, the mixture was packed into hard gelatin capsules.

PREPARATION EXAMPLE 4

(Preparation of Injections)

A 50 g quantity of Compound 11 and 400 g of glucose were successively dissolved in 8000 ml of distilled water for injection with stirring. Distilled water for injection was further added thereto to adjust the total amount to 10000 ml. The mixture was sterile-filtered, and placed into 2 ml-colorless amples. After passing nitrogen gas therethrough, the amples were sealed.

PREPARATION EXAMPLE 5

(Preparation of Suppositories)

| Compound 11 | 50 mg |
|---|---|
| Witepsol S55 (trademark, product of Dynamite Nobel, mixture of mono, di and triglycerides of saturated fatty acids ranging from lauric acid to stearic acid) | 2 g |

Witepsol S55 was heated at 120° C. for 30 minutes and cooled at room temperature to a temperature below 50° C., and mixed sufficiently with Compound 11 with stirring. The mixture was charged into a mold at about 38° C. The suppository was prepared by cooling after solidification upon cooling.

PREPARATION EXAMPLES 6 TO 20

Following the procedure of preparation Examples 1–5 and using Compounds 1, 2 and 6 in place of Compound 11, each of the preparations were formulated with the same composition.

We claim:

1. A taurine-type compound of the formula

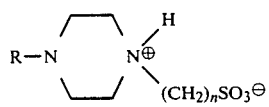 (I)

wherein R is a phenyl group unsubstituted or mono- or bi-substituted with substituent(s) selected from lower alkyl, halogen-substituted lower alkyl, lower alkoxy, lower alkanoyl and halogen atom; and n is 2 or 3.

2. A compound as defined in claim 1 wherein R is a phenyl group optionally having 1 to 2 substituents selected from $C_1$–$C_4$ alkyl, halogen-substituted $C_1$–$C_4$ alkyl, $C_1$–$C_4$ alkoxy, $C_1$–$C_4$ alkanoyl and halogen atom.

3. A compound as defined in claim 1, wherein R is a phenyl group optionally having 1 or 2 substituents selected from $C_1$–$C_4$ alkyl, $C_1$–$C_2$ alkoxy, chlorine atom and fluorine atom and n is 3.

4. A compound as defined in claim 1 which is selected from:

4-(3-sulfopropyl)-1-phenylpiperazine, inner salt, 4-(3-sulfopropyl)-1-(p-tolyl)piperazine, inner salt, 4-(3-sulfopropyl)-1-(p-isobutylphenyl)piperazine, inner salt, 4-(3-sulfopropyl)-1-(p-tert-butylphenyl)piperazine, inner salt, 4-(3-sulfopropyl)-1-(o-methoxyphenyl)piperazine, inner salt, 4-(3-sulfopropyl)-1-(m,p-dimethoxyphenyl)piperazine, inner salt, 4-(3-sulfopropyl)-1-(p-fluorophenyl)piperazine, inner salt, 4-(3-sulfopropyl)-1-(m-chlorophenyl)piperazine, inner salt and 4-(3-sulfopropyl)-1-(o-chlorophenyl)piperazine, inner salt.

5. A compound as defined in claim 1 which is selected from:

4-(3-sulfopropyl)-1-(p-tolyl)piperazine, inner salt, 4-(3-sulfopropyl)-1-phenylpiperazine, inner salt 4-(3-sulfopropyl)-1-(o-methoxphenyl)piperazine, inner salt, 4-(3-sulfopropyl)-1-(m,p-dimethoxyphenyl)piperazine, inner salt and 4-(3-sulfopropyl)-1-(p-tert-butylphenyl)piperazine, inner salt.

6. A compound as defined in claim 1 which is 4-(3-sulfopropyl)-1-(o-methoxyphenyl)piperazine, inner salt or 4-(3-sulfopropyl)-1-(p-tert-butylphenyl)piperazine, inner salt.

7. An agent for improving microcirculation containing an effective amount of a taurine-type compound of the formula

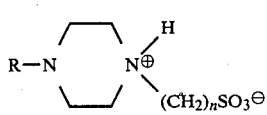 (I)

wherein R is a phenyl group unsubstituted or mono- or bi-substituted with substituent(s) selected from lower alkyl, halogen-substituted lower alkyl, lower alkoxy, lower alkanoyl and halogen atom; and n is 2 or 3, and a pharmaceutical carrier.

8. An agent for improving microcirculation as defined in claim 7 wherein R is a phenyl group optionally having 1 or 2 substituents selected from $C_1$–$C_4$ alkyl, halogen-substituted $C_1$–$C_4$ alkyl, $C_1$–$C_4$ alkoxy, $C_1$–$C_4$ alkanoyl and halogen atom.

9. An agent for improving microcirculation as defined in claim 7 wherein R is a phenyl group optionally having 1 or 2 substituents selected from $C_1$–$C_4$ alkyl, $C_1$–$C_2$ alkoxy, chlorine atom and fluorine atom and n is 3.

10. An agent for improving microcirculation as defined in claim 7 wherein the taurine-type compound is selected from:
4-(3-sulfopropyl)-1-phenylpiperazine, inner salt,
4-(3-sulfopropyl)-1-(p-tolyl)piperazine, inner salt,
4-(3-sulfopropyl)-1-(p-isobutylphenyl)piperazine, inner salt,
4-(3-sulfopropyl)-1-(p-tert-butylphenyl)piperazine, inner salt,
4-(3-sulfopropyl)-1-(o-methoxyphenyl)piperazine, inner salt,
4-(3-sulfopropyl)-1-(m,p-dimethoxyphenyl)piperazine, inner salt,
4-(3-sulfopropyl)-1-(p-fluorophenyl)piperazine, inner salt,
4-(3-sulfopropyl)-1-(m-chlorophenyl)piperazine, inner salt and
4-(3-sulfopropyl)-1-(o-chlorophenyl)piperazine, inner salt.

11. An agent for improving microcirculation as defined in claim 7 wherein the taurine-tupe compound is that selected from:
4-(3-sulfopropyl)-1-(p-tolyl)piperazine, inner salt,
4-(3-sulfopropyl)-1-phenylpiperazine, inner salt
4-(3-sulfopropyl)-1-(o-methoxypheyl)piperazine, inner salt,
4-(3-sulfopropyl)-1-(m,p-dimethoxyphenyl)piperazine, inner salt and
4-(3-sulfopropyl)-1-(p-tert-butylphenyl)piperazine, inner salt.

12. An agent for improving micorcirculation as defined in claim 7 wherein the taurin-type compound is 4-(3-sulfopropyl)-1-(o-methoxyphenyl)piperazine, inner salt or 4-(3-sulfopropyl)-1-(p-tert-butylphenyl)piperazine, inner salt.

* * * * *

UNITED STATES PATENT AND TRADEMARK OFFICE
CERTIFICATE OF CORRECTION

PATENT NO. : 4,870,078

DATED : September 26, 1989

INVENTOR(S) : ESHIMA et al

It is certified that error appears in the above-identified patent and that said Letters Patent is hereby corrected as shown below:

On the cover page, Item [54], "W-AMINO ALKYLSULFONATE DERIVATIVES FOR IMPROVING MICROCIRCULATION" should read --ω-AMINO ALKYLSULFONATE DERIVATIVES FOR IMPROVING MICROCIRCULATION--.

Column 1, lines 1 and 2, "W-AMINO ALKYLSULFONATE DERIVATIVES FOR IMPROVING MICROCIRCULATION" should read --ω-AMINO ALKYLSULFONATE DERIVATIVES FOR IMPROVING MICROCIRCULATION--.

Signed and Sealed this

Eighteenth Day of December, 1990

Attest:

HARRY F. MANBECK, JR.

*Attesting Officer*     *Commissioner of Patents and Trademarks*